Figure 1:
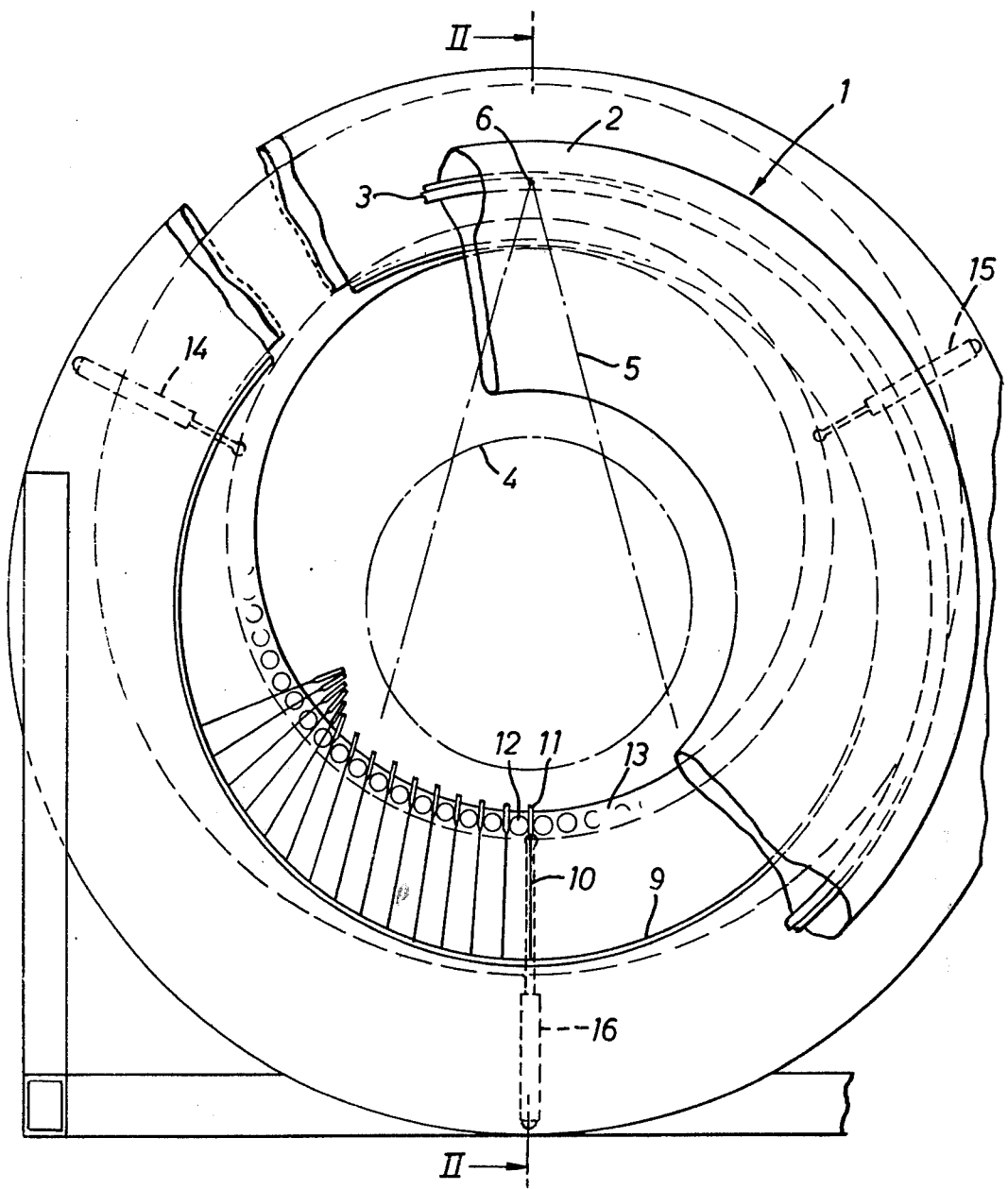

United States Patent [19]

LeMay et al.

[11] 4,126,786
[45] Nov. 21, 1978

[54] RADIOGRAPHY

[75] Inventors: Christopher Archibald G. LeMay, Osterley; Alan G. Blay, Kenley, both of England

[73] Assignee: EMI Limited, Hayes, England

[21] Appl. No.: 808,146

[22] Filed: Jun. 20, 1977

[30] Foreign Application Priority Data

Jun. 26, 1976 [GB] United Kingdom ............... 26728/76

[51] Int. Cl.$^2$ ........................ A61B 6/02; G01N 23/08
[52] U.S. Cl. .................................. 250/445 T; 250/509
[58] Field of Search ..,................ 250/445 T, 360, 508, 250/509

[56] References Cited

U.S. PATENT DOCUMENTS 4,031,395  6/1977  Le May ............................ 250/445 T

Primary Examiner—Alfred E. Smith
Assistant Examiner—T. N. Grigsby
Attorney, Agent, or Firm—Cooper, Dunham, Clark, Griffin & Moran

[57] ABSTRACT

In a computerized tomographic system in which a fan of radiation effects a rotational scan and the detectors are fixed, collimation is achieved by means of plates hinged adjacent the detectors. The plates are moved by means of a ring, the center of which is caused to execute a circular motion about the center of rotation of the system. The ring carries projections which engage with the ends of the plates remote from the detectors.

7 Claims, 4 Drawing Figures

RADIOGRAPHY

The present invention relates to radiography and it relates especially, though not exclusively, to that branch of radiography which has become known as computerised axial tomography.

The aim of computerised axial tomography is to provide a representation of the variation of absorption coefficient, with respect to the radiation (usually X-radiation) used, over a substantially planar region cross-sectionally disposed in a body under examination. Apparatus for performing computerised axial tomography is disclosed and claimed in U.S. Pat. No. 3,778,614. The technique involves projecting X-radiation through the body along a plurality of substantially co-planar paths, detecting the amount of radiation emergent from the body along each path so as to determine the absorption suffered by the radiation on traversing each path, and processing the absorption values so determined to evaluate the absorption coefficient, with respect to the radiation used, at each of a plurality of locations distributed over the irradiated region of the body.

Recent developments in the field of computerised axial tomography have lead in the direction of increasingly rapid acquisition of the data indicative of the amounts of radiation emergent from the body along the various paths. In U.S. patent application Ser. No. 668,518, filed on June 21, 1976 and now U.S. Pat. No. 4,031,395 for example, there is described an arrangement in which, in effect, a circular X-ray tube surrounds the body; the tube having an anode, coextensive therewith, over which the electron beam of the tube can be scanned electronically. It is also disclosed that a fixed, circular bank of detectors, also surrounding the body, can be used to detect the radiation. This arrangement is capable of extremely rapid acquisition of the required data, but one problem which arises is that due to the necessity for collimation of the detectors to reduce the amount of scattered radiation incident thereon.

The collimator for each detector needs to follow the motion of the source through an appreciable angle, e.g. 40°, but the motion of the souce, being caused by electronic scanning, is so rapid as to cause difficulties for a mechanical movement imparted to the collimators. It is an object of this invention to overcome or reduce such difficulties.

According to the invention there is provided radiographic apparatus including means for projecting X-radiation through a substantially planar region of a patient position from a plurality of positions disposed angularly therearound, detector means, each for detecting the radiation emergent from the patient position in sequence along a group of substantially linear paths originating from a range of said positions, and collimator means for defining said paths and shielding said detector means from scattered radiation, said collimator means being tiltable, in the plane of said region to permit radiation, originating from said range of positions, to impinge upon said detector means.

Figure 2:
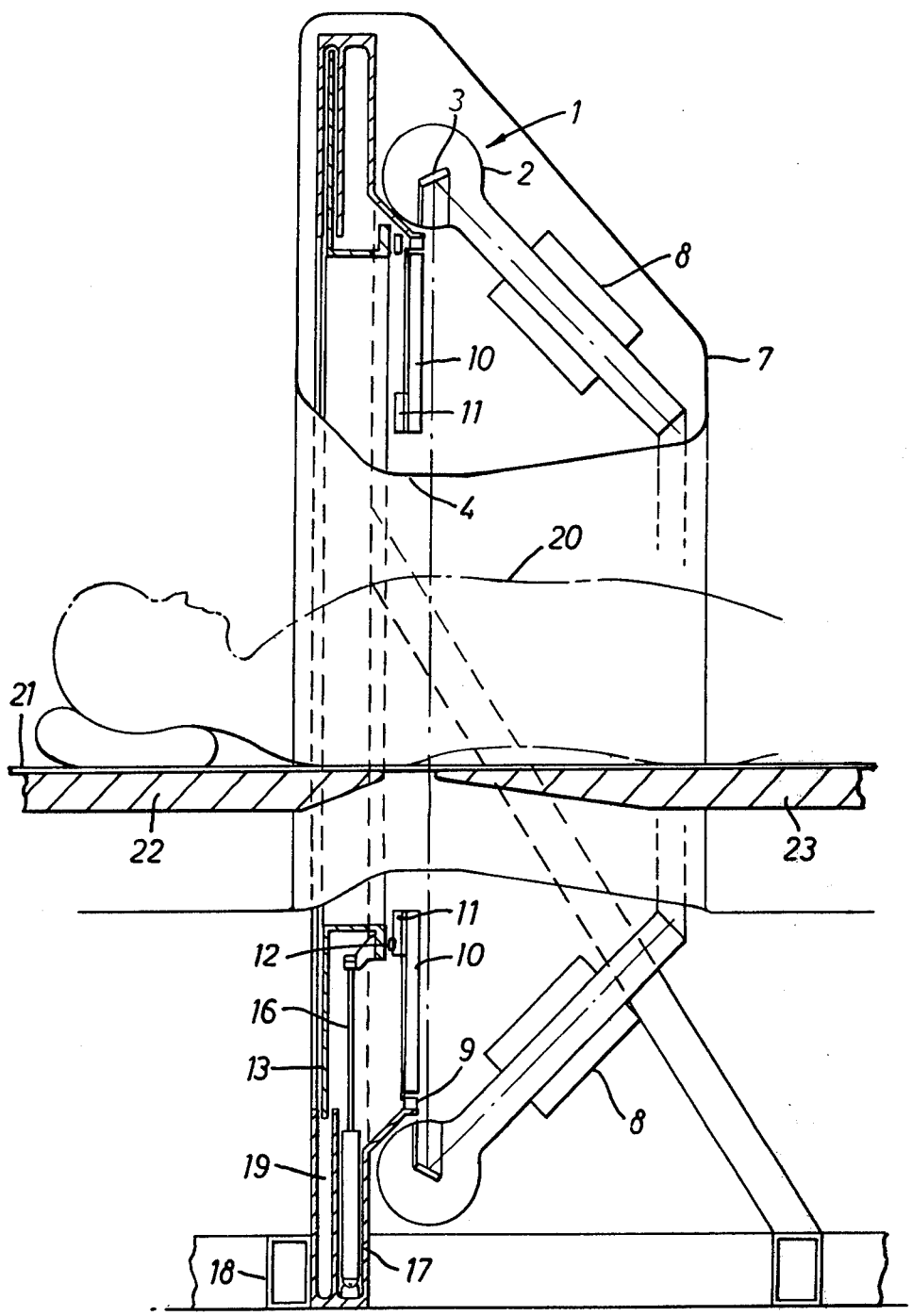

In order that the invention may be clearly understood and readily carried into effect, one embodiment thereof will now be described with reference to the accompanying drawings, of which:

FIG. 1 shows, in schematic and front elevational view, radiographic apparatus according to one example of the present invention, FIG. 2 shows, in cross-sectional view taken on arrows II—II of FIG. 1, the same radiographic apparatus, and FIG. 3 illustrates how a number of adjacent collimators can be linked together to facilitate control thereof.

Referring now to FIG. 1, the apparatus includes an X-ray tube 1 having a toroidal envelope 2 containing a fixed anode (or target) electrode 3 which completely surrounds a patient position. The patient position is within a central aperture 4 defined by a static frame member which is not shown in FIG. 1, but is shown at 7 in FIG. 2.

The anode electrode 3 is caused to project X-radiation through the patient position along a substantially planar, fan-shaped spread such as 5 from a given point (such as 6) thereon in response to the impingement, upon that point, of an electron beam. The electron beam is produced by one of a number (say eight) of cathodes equi-angularly disposed around a circle within the tube envelope 2, and the beam from each cathode can be deflected over a respective arcuate region of the anode electrode 3. In this example, where eight cathodes are used, each is designated a respective arcuate region of $(360/8)°$, i.e. 45°. The deflection is effected by means of suitable electromagnetic coils shown at 8 in FIG. 2.

A fixed, circular array 9 of radiation-sensitive detectors is disposed, around the aforementioned patient position, concentrically with the anode electrode 3. The array 9 is, however, of somewhat smaller diameter than the anode electrode, and moreover is not quite in the same plane as said anode electrode. The displacement of the planes of the anode electrode 3 and the detector array 9 is necessary, of course, to prevent obstruction of the X-rays by detectors which for the time being are not being used to provide output signals.

It will be appreciated that, with the angle of the fan-shaped spread being 30°, as shown in FIG. 1, each detector is irradiated from an arcuate sector of 30° of the anode 3. Thus each detector has to be capable of receiving radiation from a range of directions extending over 30°, but at the same time to be shielded from scattered radiation. These two requirements are difficult to meet, as they tend to be mutually incompatible, especially when rapid acquisition of data is to be effected. In this example, as the fan-shaped spread 5 of X-radiation is scanned around the body by purely electronic means, i.e. no mechanical scanning is applied to either the anode 3 or the detector array 9, the scanning is extremely rapid. For example a complete revolution of the spread 5 of radiation around the patient position can be carried out in 20mS. Thus the difficulties associated with collimating the radiation so that, at any instant, an irradiated detector can receive radiation along a straight line from the point on the anode upon which, at that time, the electron beam is impinging whilst shielding the detector from scattered radiation are acute.

It has been determined that the number of detectors required in the array 9 is 460 for a resolution of $1mm^2$ and 920 for a resolution of $\frac{1}{2}$ $mm^2$. The arrangement shown in the drawing is illustrative only and does not show the correct angular dispositions of the collimator plates referred to hereinafter. Each detector requires a collimator that is able to squint in azimuth over 30°. In accordance with this example of the invention, each collimator comprises a pair of plates 10, each plate being shared between two adjacent detectors, in the sense that it constitutes one plate of the pair of plates for each of two detectors. The collimator plates 10 are disposed radially of the system and each plate is hinged at its end closest to the detector array 9. Every eighth plate is formed with a rearwardly protruding peg 11 and this peg is dimensioned and shaped to co-operate with rollers such as 12 which protrude forwardly from a collimator guide ring 13. The ring 13 is movable, in a manner which will be more fully described hereinafter, by means of three guide ring actuators, 14, 15 and 16, which are slidably attached to the ring.

The seven collimator plates between each pair of plates provided with pegs 11 are linked to each other and to the plates provided with pegs, for example in the manner shown in FIG. 3 and which will be described in more detail hereinafter.

Referring now to FIG. 2, in which components common to FIG. 1 have been identified by the same reference numerals, it will be seen that the detector array 9 is supported by a frame member 17 which in turn, is supported by a main frame 18. The frame member 17 also contains an annular housing 19 in which the collimator guide ring 13 can move, in response to the actuators 14 to 16.

The patient, shown in schematic outline at 20, is supported on a platter 21 which can slide relative to a fixed two-part table 22, 23 and with the desired part of his body disposed so as to be irradiated by radiation projected through the patient position.

In operation, as the source of the fan-shaped spread of radiation is scanned around the body by first energising a first cathode, deflecting its electron beam over its respective arcuate portion of the anode 3 then energising a second cathode and deflecting its electron beam over its respective arcuate region of the anode 3 (the two arcuate regions being substantially contiguous) and so-on, the actuators 14–16 are operated so as to cause the centre of the collimator guide ring 13 to trace a circular locus, the locus being concentric with the anode and detector rings 3 and 9 and of diameter determined by the geometric configuration of the entire apparatus. This motion of the centre of the ring 13, properly synchronised with the scanning of the radiation around the body, causes the rollers 12 to selectively engage groups of the pegs 11 depending from selected collimator plates and, having engaged said pegs, to move the collimator plates laterally so that they pivot on their hinges and follow the movement of the source of X-rays. The rollers 12 are continuously engaging new pegs 11 and disengaging from other pegs, but each peg remains engaged with a roller 12 for long enough to squint or tilt its respective collimator plate (and those attached to it) through the angle of the fan (i.e. 30° in this case).

Figure 3A:
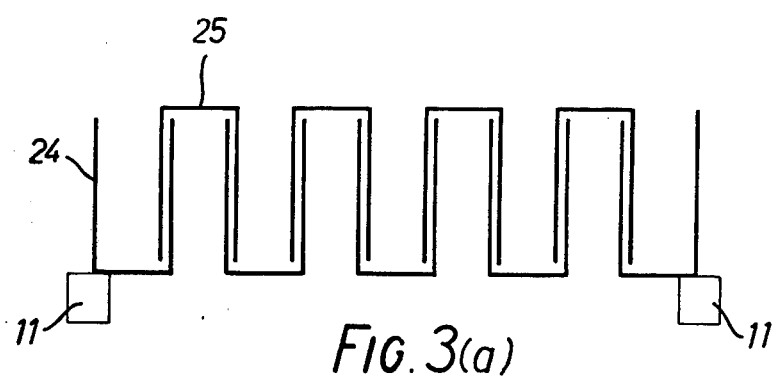

In the arrangement shown in FIG. 3, each collimator plate is made up of components of two adjacent, interlocking U-shaped members such as 24, 25. The pegs 11 are shown as attached only to the two outer members and the seven members in between are linked, via their neighbours, to the outer members, so as to move therewith. When the pegs 11 are not engaged by the rollers 12, the U-shaped members are loosely coupled, since the fact of such non-engagement means that the detectors to which those collimators appertain are not being irradiated by the spread 5 of radiation and thus are not being used, for the time being, to produce output signals indicative of the amount of radiation emergent from the body. This situation is shown in FIG. 3(a).

Figure 3B:
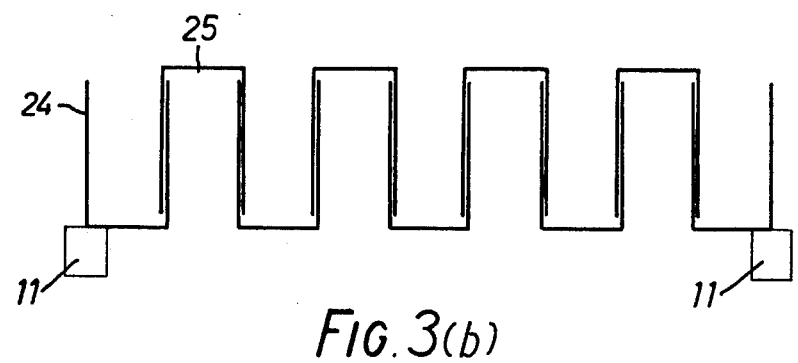

When the respective outer members have their pegs engaged by rollers 12, however, the whole group of collimator members is pulled tight, as shown in FIG. 3(b), to present accurate collimator paths to the radiation whilst the spread 5 is directed towards the respective detectors.

Other arrangements can be devised without departing from the scope of the invention. For example, each collimator plate 10 could have a peg 11 formed integrally therewith or secured thereto. In that case the rollers 12 on the guide ring 13 would have to be replaced by more compact members, and fixed pins might be used. Also, the ring 13 need not be driven in the manner shown and described hitherto. Any drive means capable of causing the centre of the ring 13 to follow the required locus can be used.

It has been found necessary to ensure either that the aforementioned pegs 11 are linked together to form a complete circuit or that buffers be provided to prevent the collimators assuming too large an angle relative to the radial position, as the assumption of such angles tends to cause jamming of the collimator system. The linking can be effected by the arrangement shown in FIG. 3 or by other means.

The pegs 11 can, if desired, be replaced with rollers of diameter equivalent to the spacing between the pegs 11 in FIG. 1, the rollers being centred on the points of attachment of pegs 11 to collimator plates 10. The rollers 12 can then be spaced apart by distances greater than those shown in FIG. 1, so as to enable them to engage with, and move, the larger rollers attached to the collimator plates 10. The large rollers have to be linked together, or buffers have to be provided, for the same reasons as described above with respect to pegs 11.

What we claim is:

1. Radiographic apparatus including means for projecting X-radiation through a substantially planar region of a patient position from a plurality of positions disposed angularly therearound, detector means, each for detecting the radiation emergent from the patient position in sequence along a group of substantially linear paths originating from a range of said positions, and collimator means for defining said paths and shielding said detector means from scattered radiation, said collimator means being tiltable, in the plane of said region to permit radiation, originating from said range of positions, to impinge upon said detector means.

2. Apparatus according to claim 1 wherein said collimator means includes a plurality of plate members protruding from the detector means toward said patient position, a pair of said plate members flanking each individual detector, and said plate members being hinged at their ends adjacent said detector means to permit the tilting to occur.

3. Apparatus according to claim 2 wherein at least some of said plate members are formed with pegs at their ends remote from said detector means and a collimator guide ring is provided which contains roller members adapted to co-operate with said pegs.

4. Apparatus according to claim 3 including means for moving said collimator guide ring, so that the locus of said ring traces a circle, in synchronism with movement of the X-radiation relative to the patient position.

5. Apparatus according to claim 3 wherein plate members intermediate those formed with pegs are all interlined with each other and with the members formed with pegs.

6. Apparatus according to claim 5 including means for moving said collimator guide ring, so that the locus of said ring traces a circle, in synchronism with movement of the X-radiation relative to the patient position.

7. Medical radiographic apparatus comprisng a source of X-radiation fanning out from a point, means defining a patient position at which a cross-sectional slice of a patient's body to be examined can be disposed, means for scanning said point around said patient position to irradiate said slice from a plurality of locations angularly distributed therearound, detector means including an array of detector devices extending at least half-way around said patient position, said devices being fixed in angle in the plane of said slice, and collimator means positioned between said patient position and said detector devices to permit radiation to traverse direct linear paths from said point through said patient position to said detector devices but to obstruct scattered radiation which could otherwise impinge on said detector devices, the collimator means comprising plate members flanking each detector and protruding toward said point, and drive means for parting the plate members associated with each detector device for the time being irradiated with said X-radiation and for tilting said last-mentioned plate members to follow the scanning of said point until the scanning has moved the point so that the respective detector device is no longer irradiated and thereafter permitting adjacent plate members to collapse toward one another.

* * * * *